(12) United States Patent
Cawthon et al.

(10) Patent No.: US 9,827,369 B2
(45) Date of Patent: Nov. 28, 2017

(54) PERCUTANEOUS ADMINISTRATION DEVICE AND METHOD FOR INJECTING MEDICINAL SUBSTANCES

(71) Applicants: BAXTER INTERNATIONAL INC., Deerfield, IL (US); BAXTER HEALTHCARE S.A., Glattpark (Opfikon) (CH)

(72) Inventors: Dustin Christopher Cawthon, Crystal Lake, IL (US); Yuanpang Samuel Ding, Long Grove, IL (US)

(73) Assignees: BAXTER INTERNATIONAL INC., Deerfield, IL (US); BAXTER HEALTHCARE S.A., Glattpark (Opfikon) (CH)

( * ) Notice: Subject to any disclaimer, the term of this patent is extended or adjusted under 35 U.S.C. 154(b) by 63 days.

(21) Appl. No.: 15/071,853

(22) Filed: Mar. 16, 2016

(65) Prior Publication Data

US 2017/0266369 A1    Sep. 21, 2017

(51) Int. Cl.
    *A61M 5/32*      (2006.01)
    *A61M 5/142*     (2006.01)
    *A61K 9/70*      (2006.01)

(52) U.S. Cl.
    CPC ....... *A61M 5/14248* (2013.01); *A61K 9/7038* (2013.01); *A61M 2005/14252* (2013.01)

(58) Field of Classification Search
    CPC .......... A61M 2005/1581; A61M 5/158; A61M 2005/1585; A61M 2005/1587; A61M 5/14248; A61M 2005/14252; A61M 5/3287; A61M 5/1413
    USPC ....... 604/93.01, 131, 136, 164.01, 174, 180, 604/192, 263, 264, 272, 506
    See application file for complete search history.

(56) References Cited

U.S. PATENT DOCUMENTS

| | | |
|---|---|---|
| 3,538,915 A | 11/1970 | Frampton et al. |
| 3,640,275 A | 2/1972 | Burke et al. |
| 4,129,128 A | 12/1978 | McFarlane |
| 4,380,234 A | 4/1983 | Kamen |
| 4,710,176 A | 12/1987 | Quick |

(Continued)

FOREIGN PATENT DOCUMENTS

| | | |
|---|---|---|
| GB | 2014045 A | 8/1979 |
| WO | 2000074763 A2 | 12/2000 |
| WO | 2007137339 A1 | 12/2007 |

*Primary Examiner* — Gerald Landry, II
(74) *Attorney, Agent, or Firm* — Greer, Burns & Crain, Ltd.

(57) ABSTRACT

A medical delivery device is provided for delivering a medicinal substance into a user's body. An upper assembly includes a housing having a cavity configured for accommodating a needle. A lower assembly includes a receptacle member having an opening configured for accommodating insertion of the upper assembly, and a base member having an upper body and a recess formed on a top surface of the upper body for receiving the receptacle member. A base pad has an adhesive layer disposed on a lower surface of the pad, and being at least partially attached to a bottom side of the base member. The lower assembly is attached to a skin of the user using the base pad. As the upper assembly transitions from an upper position to a lower position relative to the lower assembly, the needle travels downwardly to penetrate the skin for facilitating administration of the medicinal substance.

20 Claims, 4 Drawing Sheets

(56) References Cited

U.S. PATENT DOCUMENTS

| | | | |
|---|---|---|---|
| 4,886,499 A * | 12/1989 | Cirelli | A61M 5/142 128/DIG. 12 |
| 5,176,662 A | 1/1993 | Bartholomew et al. | |
| 5,257,980 A | 11/1993 | Van Antwerp et al. | |
| 5,584,813 A | 12/1996 | Livingston et al. | |
| 5,848,990 A * | 12/1998 | Cirelli | A61M 5/158 604/131 |
| 6,254,586 B1 | 7/2001 | Mann et al. | |
| 6,572,586 B1 | 6/2003 | Wojcik | |
| 6,685,674 B2 * | 2/2004 | Douglas | A61M 5/158 604/167.05 |
| 6,960,192 B1 * | 11/2005 | Flaherty | A61M 5/14248 604/131 |
| 7,150,726 B2 | 12/2006 | Dalton | |
| 8,162,892 B2 * | 4/2012 | Mogensen | A61M 5/158 604/157 |
| 8,303,549 B2 * | 11/2012 | Mejlhede | A61M 5/142 604/180 |
| 8,532,567 B2 | 9/2013 | Moeglein et al. | |
| 8,814,831 B2 * | 8/2014 | Constantineau | A61M 5/158 604/164.01 |
| 9,067,010 B2 * | 6/2015 | Schraga | A61M 5/14248 |
| 9,408,984 B2 * | 8/2016 | Durack | A61M 5/282 |
| 2003/0060781 A1 | 3/2003 | Mogensen | A61M 5/158 604/257 |
| 2003/0187423 A1 | 10/2003 | Wilkinson et al. | |
| 2003/0212362 A1 * | 11/2003 | Roser | A61M 5/282 604/110 |
| 2004/0019327 A1 * | 1/2004 | Metzger | A61M 5/158 604/157 |
| 2004/0158207 A1 * | 8/2004 | Hunn | A61M 5/158 604/164.01 |
| 2005/0283114 A1 * | 12/2005 | Bresina | A61M 5/158 604/93.01 |
| 2006/0047252 A1 | 3/2006 | Ono | |
| 2006/0058431 A1 * | 3/2006 | Cartier | C08K 5/3492 524/115 |
| 2006/0069351 A9 * | 3/2006 | Safabash | A61M 5/158 604/136 |
| 2007/0118081 A1 * | 5/2007 | Daily | A61M 5/326 604/198 |
| 2007/0135774 A1 * | 6/2007 | Turner | A61K 9/0019 604/288 |
| 2008/0269687 A1 * | 10/2008 | Chong | A61L 15/58 604/180 |
| 2009/0216215 A1 * | 8/2009 | Thalmann | A61M 5/158 604/506 |
| 2009/0270804 A1 * | 10/2009 | Mesa | A61M 5/2033 604/111 |
| 2009/0299302 A1 * | 12/2009 | Lambert | A61M 5/158 604/263 |
| 2010/0049129 A1 * | 2/2010 | Yokoi | A61M 5/158 604/136 |
| 2010/0217105 A1 * | 8/2010 | Yodfat | A61B 5/14503 600/365 |
| 2012/0184907 A1 * | 7/2012 | Smith | A61M 5/14248 604/152 |
| 2012/0323183 A1 * | 12/2012 | Peterson | A61M 5/14248 604/180 |
| 2013/0218129 A1 | 8/2013 | Clarke et al. | |
| 2013/0237961 A1 | 9/2013 | Pettis et al. | |
| 2015/0025338 A1 * | 1/2015 | Lee | A61B 5/14503 600/309 |
| 2017/0246428 A1 * | 8/2017 | Constantineau | A61M 25/0606 |

* cited by examiner

PERCUTANEOUS ADMINISTRATION DEVICE AND METHOD FOR INJECTING MEDICINAL SUBSTANCES

BACKGROUND

The present disclosure generally relates to devices for injecting medicinal substances, and more particularly relates to a medical fluid delivery device for percutaneously administering liquid medicines into the body of a user.

Percutaneous or subcutaneous infusion devices are well known in the medical arts for use in the administration of a selected medicinal substance to a desired infusion site located underneath the skin of a patient or user. Commonly included in conventional infusion devices is a tubular cannula or catheter that is supported by and protrudes from a hub for receiving the medicinal substance via a delivery tubing. Typically, the hub includes a small needle that is inserted just under the surface of the skin, and remains in place for up to several hours or even days.

More specifically, such infusion devices provide an alternative to intravenous (IV) delivery of medicines and allow the medicinal substance to be administered through a layer of skin immediately below the dermis and epidermis. As is known in the art, such use of subcutaneous infusion devices decreases the number of times the patient must receive frequently administered medicines by injection. Although not all medicines can be administered through such infusion devices, they are an effective and convenient way to administer medicinal substances without having to impose multiple injections on the patient.

Due to rising expenses related to a hospital stay and other factors, many patients prefer to administer the medicinal substances at their homes or care facilities. Choosing a home care regimen is relatively economical and convenient for the patients. However, many conventional infusion devices are designed for use by skilled clinicians in a hospital environment. These conventional infusion devices tend to be complex, and require specific techniques for setting up and maintaining the device. When implementing a home care infusion regimen, patients and caregivers need to take special care to maintain sanitary conditions, and to follow treatment protocols.

Most percutaneous infusion devices are designed for use in the hospital environment only by skilled clinicians. Moreover, conventional infusion devices are not favored for self-administration because the patients must follow a series of complex steps to prepare the infusion device, such as preparing the skin for insertion, and inserting and securing the needle properly on the skin. These steps require skilled techniques because, when the needle is inserted too deep, the infusion device delivers the medicinal substance into the muscle tissue rather than the adipose tissue, causing pain and inadequate uptake of the medicinal substance. In addition, if the needle is not inserted deep enough, the infusion device delivers the medicinal substance into the outer layers of the dermal tissue, causing tissue swelling and leakage of the medicinal fluid.

Further, even before the self-administration, many patients become fearful of the needle because the needle is readily visible. Moreover, before and after use of an infusion device having a needle, the pointed tip of the needle may be exposed thereby raising the risk of needlestick injury.

Therefore, there is a need for improving percutaneous or subcutaneous infusion devices to facilitate a less complex process for preparing, attaching, and securing the device to the skin, for reducing fear associated with use of the device during the insertion step, and for preventing needlestick injury.

SUMMARY

The present disclosure is directed to a medical fluid delivery device for subcutaneously administering liquid medicines into the body of a user or patient. The present infusion device has a lower assembly and an upper assembly, wherein the lower assembly is configured to be removably attached to a skin of the patient at an administration or infusion site, and the upper assembly is configured to be moveably connected to the lower assembly.

A needle is included in the upper assembly for penetrating outer layers of the skin for facilitating administration of medical substances from the medical container into a subcutaneous tissue of the patient.

An important aspect of the present infusion device is that the needle is substantially enclosed by the present device, so that the needle is invisible to the patient or user and needlestick injury is avoided. In this configuration, the patient or user can activate the present infusion device without watching the needle penetrating the skin. Further, upon the activation of the present infusion device, when a releasable locking mechanism of the present infusion device is engaged, the needle remains penetrating the skin to allow time for infusion.

During the insertion, the needle remains stable and straight in the upper assembly for preventing needle breakage due to undesirable movement of the upper assembly. Under a user initiated action, the needle promptly and conveniently penetrates into the skin without requiring much time or manipulative skill. Thus, the patient or user can easily deploy the needle without the help of a skilled clinician in the hospital environment.

Another aspect of the present infusion device is that the lower assembly delivers at least one first active substance to the skin prior to engagement of the upper assembly for preparing the skin for penetration. To improve efficacy of the present device, the lower assembly also delivers a second active substance to the skin during the administration of the medical substance for enhancing general health of the skin at or near the infusion site.

In one embodiment, a medical delivery device is provided for delivering a medicinal substance into a user's body. An upper assembly includes a housing having a cavity configured for accommodating a needle. A lower assembly includes a receptacle member having an opening configured for accommodating insertion of the upper assembly, and a base member having an upper body and a recess formed on a top surface of the upper body for receiving the receptacle member. A base pad has an adhesive layer disposed on a lower surface of the pad, and being at least partially attached to a bottom side of the base member. The lower assembly is attached to a skin of the user using the base pad. As the upper assembly transitions from an upper position to a lower position relative to the lower assembly, the needle travels downwardly to penetrate the skin for facilitating administration of the medicinal substance.

DETAILED DESCRIPTION

Figure 1:
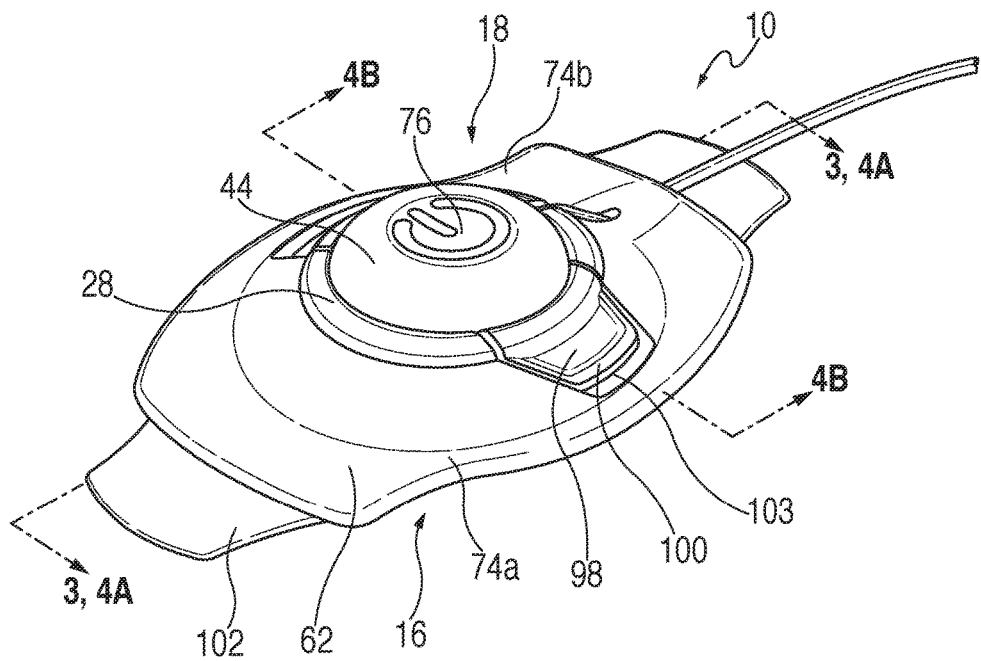
FIG. 1 is a perspective view of the present infusion device, featuring a lower assembly and an upper assembly.

Referring now to FIGS. 1-3, and 6, the present percutaneous or subcutaneous infusion device is generally designated 10 and is designed for subcutaneously delivering a medicinal substance below a skin 12 having dermis and epidermis tissues of a patient 14. An exemplary medicinal substance may include commercial pharmaceuticals, nutritional products and Chinese herbal medicinal products. It is contemplated that the device 10 is disposable, but a reusable configuration for a predetermined number of times or period is also contemplated to suit different applications.

Included in the device 10 are a lower assembly, generally designated 16, and an upper assembly, generally designated 18, wherein the lower assembly is configured to be removably attached to the skin 12 of the patient 14 at a desired administration or infusion site, and the upper assembly is configured to be releasably connected to the lower assembly. While a generally round shape when viewed from above is shown for the lower and upper assemblies 16, 18, other geometric shapes, such as rectangular, square, hexagonal, oval shapes, and the like, are contemplated to suit the application.

Before use, the desired infusion site of the skin 12 is sanitized and cleansed in preparation of attachment of the present device 10. It is preferred that an adhesive layer 22 is attached to a bottom portion 26 of the lower assembly 16, such that the present device 10 is removably attached to the skin 12 of the patient 14 using the adhesive layer during use. In one embodiment, the adhesive layer is provided in a pad format and is inserted into a base pad recess 20 disposed on the bottom portion 26 for facilitating secure attachment to the lower assembly 16. It is contemplated that the adhesive layer 22 is made of a material that is soft, flexible, and biocompatible for use on the skin 12 of the patient 14.

After firm attachment of the present device 10 to the skin 12, activation of the present device 10 is readily achieved by downwardly depressing the upper assembly 18 toward the skin along an axis substantially transverse to a plane defined by a bottom surface 72. Thus, the upper assembly 18 transitions from an upper position to a lower position relative to the lower assembly 16. It is contemplated that the adhesive layer 22 and/or bottom surface 72 includes and gradually releases at least one first active substance, such as antiseptic agents or anesthetics, to the skin 12 for preparing the skin for penetration prior to activation of the present device 10.

Further, depending on a type of therapy or environment for the patient 14, to improve efficacy of the present device 10, the adhesive layer 22 and/or bottom surface 72 may include and gradually release a second active substance, such as analgesics, skin permeation enhancers, and skin conditioning agents, to the skin 12 during the administration of the medical substance for enhancing general health of the skin at or near the infusion site.

Figure 3:
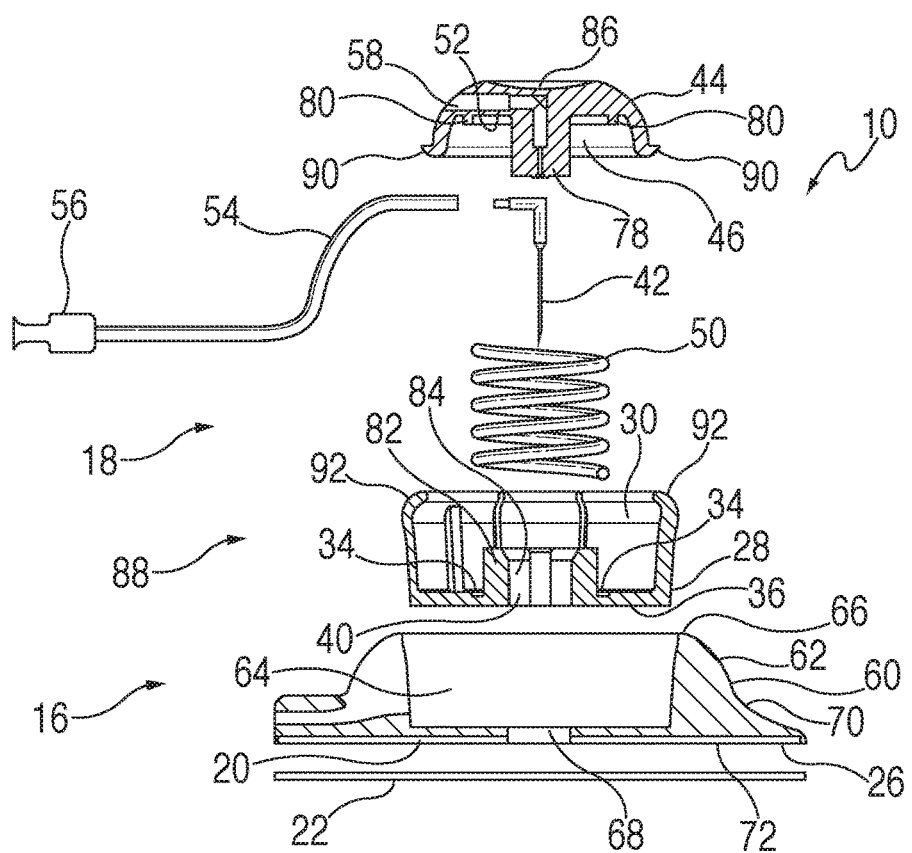
FIG. 3 is an exploded vertical cross-section of the present infusion device, taken along the line 3-3 of FIG. 1 and in the direction generally indicated.

As best shown in FIG. 3, also included in the lower assembly 16 is a receptacle member 28 having an opening 30 configured for accommodating insertion of the upper assembly 18.

A first central channel or throughbore 40 is disposed at a center of the bottom side 36 of the receptacle member 28, and is dimensioned to slidingly receive a needle 42 disposed in the upper assembly 18. The needle 42 penetrates the outer layers of the skin 12 for facilitating administration of the medical substance into the subcutaneous tissue of the patient 14. It is preferred that the needle 42 has a thin tubular wall for accommodating the delivery of the medicinal substance.

It is preferred that the upper assembly 18 includes a housing 44 that is operatively attached to the needle 42 whereby a displacement of the housing results in an operational displacement of the needle. A biasing member 50 engages and produces opposing forces on the housing 44 and lower assembly 16. In an embodiment the biasing member 50 is a coiled spring; however, other suitable types of biasing mechanisms as known in the art, such as metallic helical coils, are contemplated. It is preferred that the biasing member 50 is dimensioned to fit in the opening 30 of the receptacle member 28 and a cavity 46 of the housing 44, such that the member is extendable and collapsible with the opening and cavity, and exerts opposing biasing forces on an inner surface 34 of the bottom side 36 of the receptacle member and a top inner surface 52 of the housing.

It is contemplated that a flexible elongated tube 54 is connected at one end to an upper end of the needle 42 (i.e., an opposite end of a sharp end of the needle), and at an opposite end to a luer 56 in fluid communication with a container (not shown). The connection of the upper end of the needle 42 to the tube 54 occurs within a passage channel 58 formed by and within the housing 44.

In a preferred embodiment, the passage channel 58 is formed to extend inward from an outer circumference of the housing 44, and the tube 54 is slidingly inserted into the channel 58 to be connected to the needle 42

Referring now to FIGS. 3, 4A, 4B, 5A, and 5B, it is preferred that the lower assembly 16 includes a base member 60 having an elongated and substantially dome-shaped body 62. A crater-like recess 64 is formed within the base 60 and extends downward from a top surface 66 of the body and is configured for receiving the receptacle member 28. For example, the receptacle member 28 is secured in the recess 64 by a friction fit, or an adhesive. The base 60 also forms a second central throughbore 68 extending downward through the base 60 from a bottom of the recess 64. It is contemplated that the recess 64 and throughbore 68 of the base 60 of the device 10 is configured and dimensioned such that upon accommodating the insertion of the receptacle member 28, the first throughbore 40 of the receptacle member 28 is aligned with the second throughbore 68 of the base member 60 to allow movement of the point of the needle 42 therethrough.

The top surface 66 of the upper body 62 has an annular sloped region 70 formed around the recess. It is preferred that the dome-shaped upper body 62 is made of a flexible material, such as polyurethane foam, but the receptacle member 28 is made of a rigid material, such as polypropylene or ABS (acrylonitrile butadiene styrene). However, other suitable materials are contemplated as known in the art.

To provide a larger contact area with the skin 12, the adhesive layer 22 is attached to the bottom surface 72 of the body 62. It is preferred that the layer 22 completely covers the bottom surface 72. Advantageously, enhanced support is provided for the device 10 from unwanted movement because the adhesive layer 22 grips a larger area of the skin 12 while the housing 44 and the receptacle member 28 are securely held in the recess 64. It is preferred that at least one side of the adhesive layer 22 protrudes beyond an outer circumference of the upper body 62 for providing an enhanced gripping power to the base member 60. For example, as illustrated in FIGS. 1 and 2, opposite portions of the adhesive layer 22 extend beyond the outer circumference of the upper body 62 relative to a longitudinal axis of the body, such that the device 10 is readily removed by holding one of the extended portions of the adhesive layer.

Figure 2:
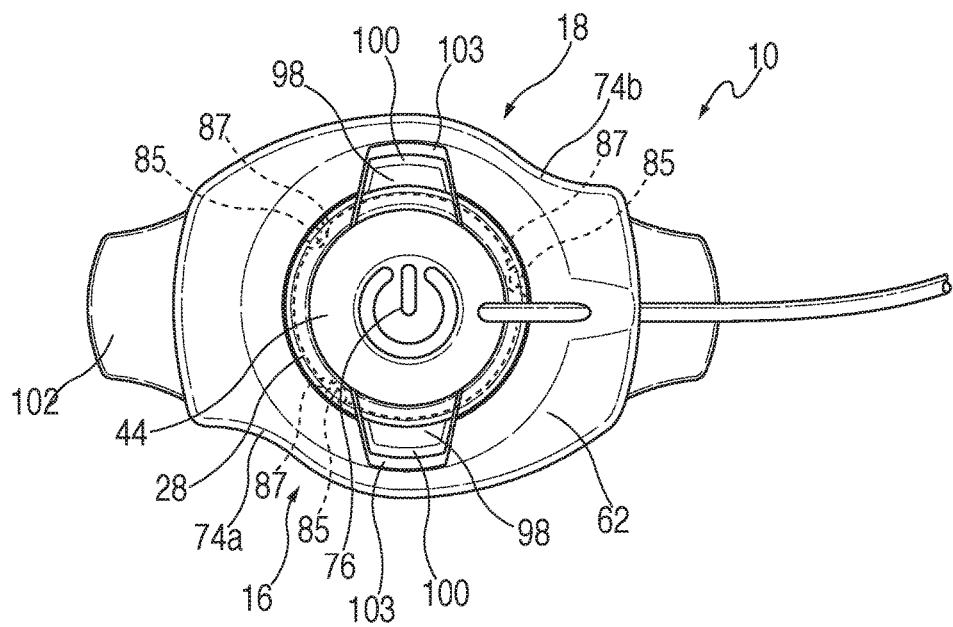
FIG. 2 is a plan view of the present infusion device of FIG. 1.

As best shown in FIGS. 1 and 2, it is preferred that the upper body 62 forms a set of ergonomically shaped opposite scalloped indents 74a, 74b configured for providing extra comfort and non-slip grip and control during handling of the device. It is contemplated that the indents 74a, 74b are formed along the outer circumference of the upper body 62 in an opposite direction relative to a center point 76 of the device 10. For example, as shown in FIG. 2, a first indent 74a is formed to extend along a lower left corner of the upper body 62, and an opposite second indent 74b is formed to extend along an upper right corner of the upper body 62, wherein both indents are positioned in the opposite direction relative to the center point 76. This configuration of the upper body 62 provides enhanced attachment to the skin 12 and reduces needle movement during use. Specifically, this specific geometry of the upper body 62 provides an improved surface area for adhesion, and preferably thin, web-like outer edges of the upper body are intended to move with the skin 12 and prevent forces applied to the body from being transferred directly to the needle 42.

Returning to FIGS. 2, 3, 4A, 4B, 5A, and 5B, a cylindrical column 78 extends transversely from the top inner surface 52 of the housing 44, and is configured for enclosing at least a portion of the needle 42. To provide support for the biasing member 50, an axially oriented, depending annular rib 80 is disposed on the top inner surface 52 of the housing 44 for receiving and positionally engaging a top portion of the member 50. A tubular column 82, dimensioned to extend within a central opening of the spring 50, extends upwardly from the inner surface 34 of the bottom side 36. Specifically, the tubular column 82 extends upwardly transverse to the bottom side 36 at approximately one-half the height of the receptacle member 28 for supporting the biasing member 50. In this configuration, the channel or throughbore 40 is defined by an inner wall 84 of the tubular column 82, and is dimensioned to slidingly receive the cylindrical column 78 of the housing 44.

It is also contemplated that the tubular column 82 and cylindrical column 78 contain one or more keyed ribs to orient the columns 78, 82 and ensure smooth axial movement upon activation of the device 10, thereby reducing twisting and/or rocking motion of the lower and upper assemblies 16, 18. As best shown in FIG. 2, it is preferred that a perimeter guide rib 85 (shown hidden) is vertically disposed on an inner surface of the receptacle member 28, and a corresponding housing groove 87 (also shown hidden) is disposed on an outer periphery of the housing 44. In use, the perimeter guide rib 85 is matingly slidingly inserted into the corresponding groove 87, such that the housing 44 is guided during vertical reciprocal transitions between an upper position and a lower position relative to the receptacle member 28.

Figure 4A:
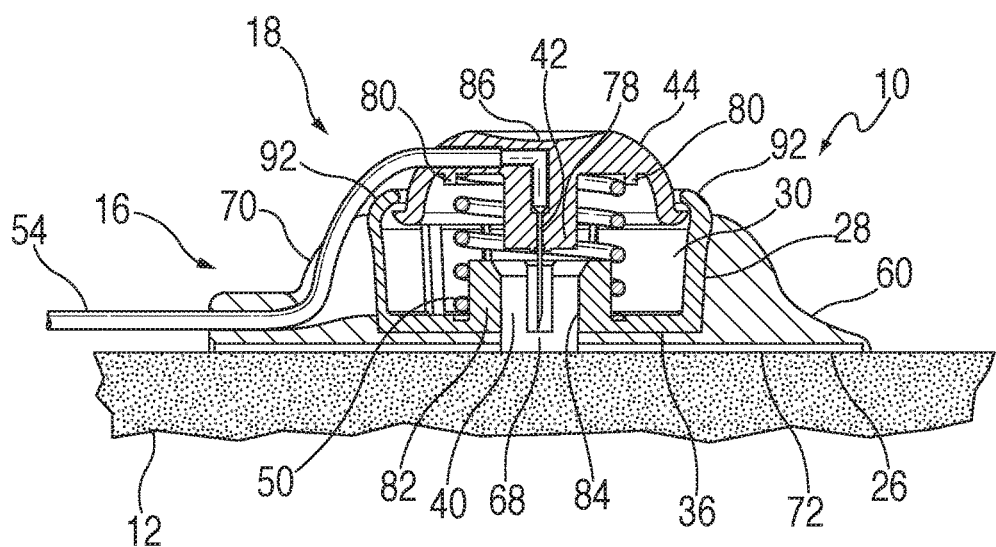
FIG. 4A is a vertical cross-section of the present infusion device, taken along the line 4A-4A of FIG. 1 before activation and in the direction generally indicated.
Figure 4B:
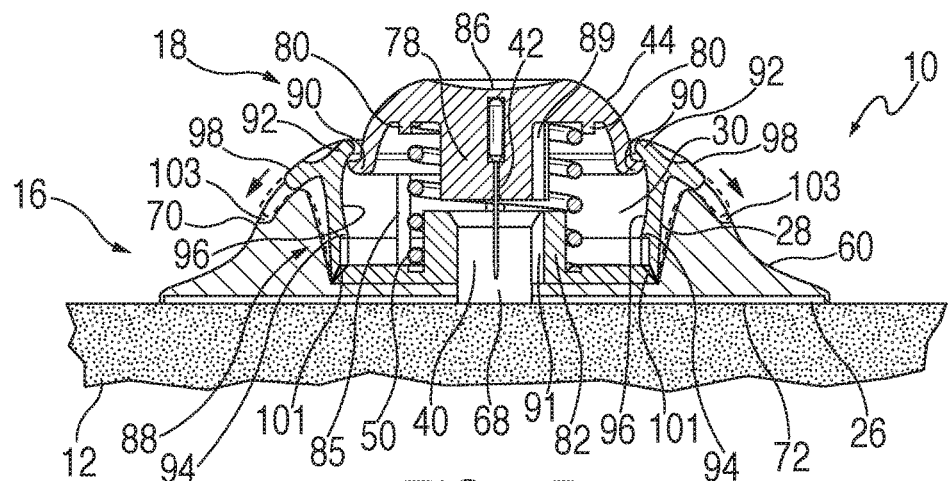
FIG. 4B is a vertical cross-section of the present infusion device, taken along the line 4B-4B of FIG. 1 before activation and in the direction generally indicated.

Further, as best shown in FIG. 4B, it is preferred that at least one cylindrical column guide rib 89 is vertically disposed on an outer surface of the cylindrical column 78, and a corresponding at least one tubular column groove 91 is vertically disposed on an inner surface of the tubular column 82. In use, a plurality of the cylindrical column guide ribs 89 are matingly slidingly inserted into the corresponding tubular column grooves 91, such that the housing 44 is guided during the reciprocal vertical transitions between the upper and lower positions relative to the receptacle member 28.

An indented press button 86 (FIG. 3) is disposed at the top center of the housing 44 of the upper assembly 18, to form a surface for the user to apply the downward driving force to actuate the present device 10.

Figure 5A:
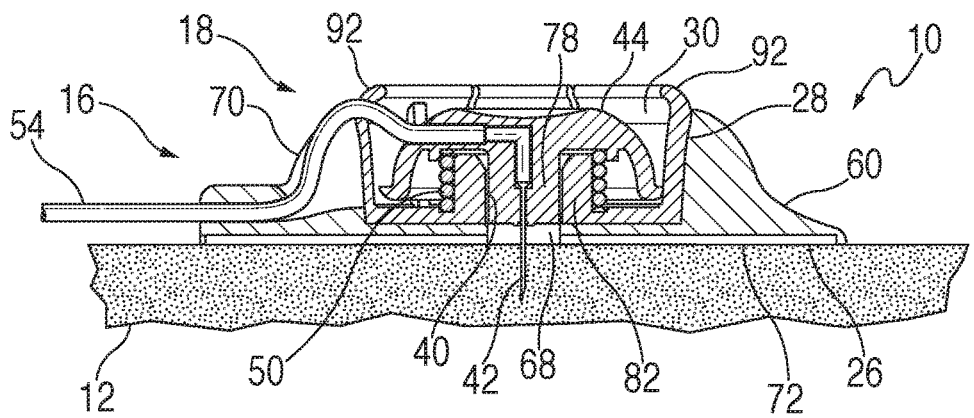
FIG. 5A is a vertical cross-section of an alternate embodiment of the present infusion device of FIGS. 1-4A after activation.
Figure 5B:
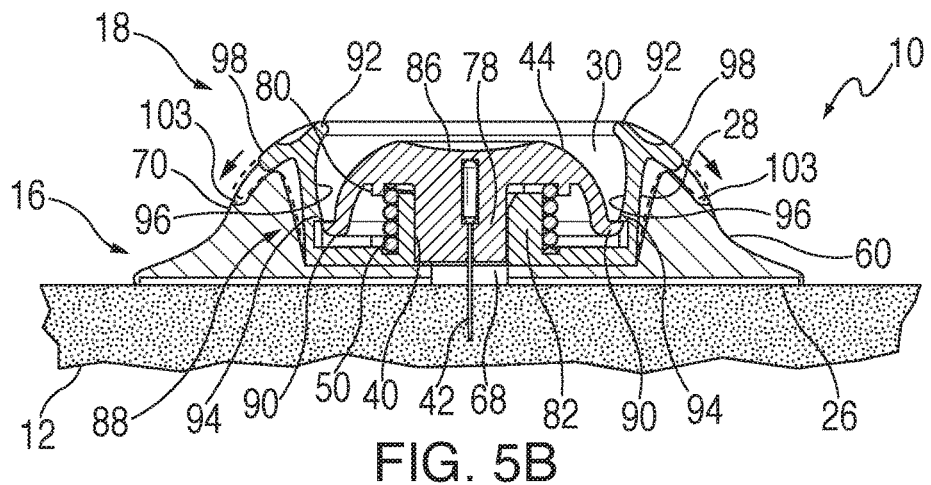
FIG. 5B is a vertical cross-section of the device of FIG. 4B after activation.

As best shown in FIGS. 3, 4B and 5B, for securely attaching the upper assembly 18 to the lower assembly 16, a snap-fit locking mechanism, generally designated 88, is provided in the present infusion device 10, and configured for releasably connecting the assemblies 16, 18 together. Included in the locking mechanism 88 is a first annular flange or lip 90 formed by the housing 44 to extend outwardly relative to a longitudinal axis of the cylindrical column 78 so as to form the lower outer circumference of the housing 44. The receptacle member 28 forms a second annular flange or lip 92, extending inwardly from an upper outer circumference of the receptacle member relative to the longitudinal axis of the tubular column 82. In an unactivated state of the device 10, the first flange 90 and the second flange 92 of the locking mechanism 88 are engaged for securely holding the lower and upper assemblies 16, 18 together (FIG. 4B).

More particularly, while the biasing member 50 simultaneously and opposingly biases the inner surface 34 of the bottom side 36 of the receptacle member 28 and the inner surface 52 of the housing 44, the housing is securely held in the crater-like recess 64 of the receptacle member by the first and second annular flanges 90, 92 in a mechanically complementary manner. At this point, the housing 44 is freely movable within the opening 30 of the receptacle member 28 when the depressing force is applied on the button 86.

Referring to FIG. 2 along with FIG. 4B, the receptacle 28 is formed with two opposing outwardly bendable wing segments 98 with the lateral edges of the wing segments formed by pairs of slits 101 that extend through the annular wall of the receptacle 28 and downward from the lip 92 to the inner surface 34 of the receptacle. It is preferred that surfaces of the wing segments 98 are reduced in thickness toward the bottom side 36 of the receptacle member 28, and the connection of the wing segments to the inner surface 34 of the bottom side of the receptacle member is scored along a lower edge of the corresponding wing segment, thereby forming a curved, radial scoring line as a living hinge between the slits 101.

As best viewed in FIG. 4B, a downward directed force applied on the wing segments 98 causes the wing segment to flex outward into a flexing cavity 103 formed by the base 60. Releasing such a force allows the wing segment 98 to recover inwardly to its initial configuration. Extending along an inner annular surface of the wing segment is a lower locking tab 94. Inward and outward flexing of the wing segments 98 also causes a corresponding movement of this locking tab 94.

As seen in FIG. 4A, prior to activation, the point of the needle 42 is securely encased within throughbore 40 to prevent needlesticks. Moreover, the needle is hidden from the user to lessen apprehension regarding the upcoming insertion.

For activation of the device 10, the button 86 of the housing 44 is depressed downwardly by the user toward the skin 12 against the biasing force of the member 50. As the housing 44, guided by the tubular column 82 within the throughbore 40, travels downwardly within the throughbore of the receptacle member 28, the first annular flange 90 engages and pushes outwardly the locking tab 94 disposed on an inner surface of a side wall 96 (FIGS. 4B and 5B) of the receptacle member 28.

As seen in FIGS. 4B and 5B, because the wing segments 98 can flex outwardly into the cavity 103 (illustrated in phantom in directions indicated by arrows), the outward pushing force caused by a downward movement of the housing 44 by the user causes the wing segments to flex outwardly, thereby providing a corresponding outward displacement of the locking tab 94 to allow the continued downward movement of the flange 90 and housing 44. After the first annular flange 90 travels downward past the locking tab 94 to release the outward force, the wing segments 98 and locking tabs 94 resiliently return back to their original positions.

During this movement, the pointed end of the needle 42 travels downward and penetrates the skin 12 through the first and second throughbores 40, 68 for the delivery of the medicinal substance. A preferred range of the insertion length is between 5 and 6 millimeters past the throughbore 40, which ensures that the sharp end of the needle 42 is positioned deeply into the subcutaneous tissue, and accounts for the variability in the adipose layer of the patient 14 at the infusion site. While a straight needle is shown for illustration purposes, other suitable types of needles used for the infusion therapy are contemplated.

Upon the release of the downward pressing force on the housing 44 by the user, the biasing force of the member 50 continues to push and thereby displace the housing upward; however, the locking tab 94 and flange 90 engage to prevent further upward movement of the housing to maintain the needle 42 in the preferred insertion depth for the duration of the infusion.

For releasing the housing 44 after infusion has been completed, the user applies a downward pushing force on the associated wing regions 98 (FIGS. 1 and 2). At least one ridge or projection 100 (FIGS. 1 and 2) is disposed on the wing region 98 for providing enhanced gripping. This force causes an outward flexing of the wing region 98 into the cavity 103 and also causes a resulting outward movement of the locking tab 94 such that the first flange 90 is released from the locking tab 94. As a result of the release of the engagement between the locking tab 94 and flange 90, the housing 44 is pushed upwardly under the action of the biasing member 50 until the first flange 90 is again engaged and stopped by the second flange 92 of the receptacle member 28 (FIG. 4B). The point of the needle 42 is returned to being housed within the throughbore 40 to prevent needlesticks upon removal of the device 10 from the user.

Figure 6:
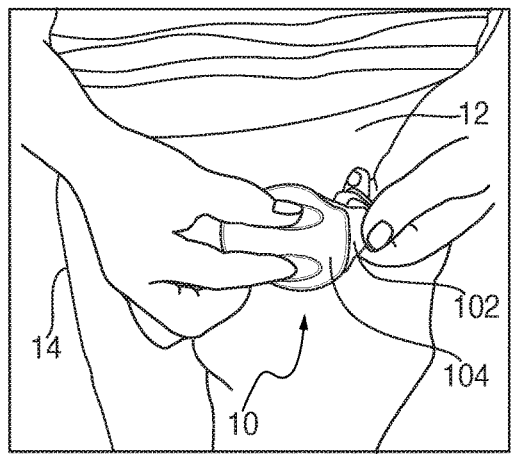
FIGS. 6-9 illustrate an exemplary method of using the present infusion device of FIG. 1 in accordance with an embodiment of the present disclosure.
Figure 7:
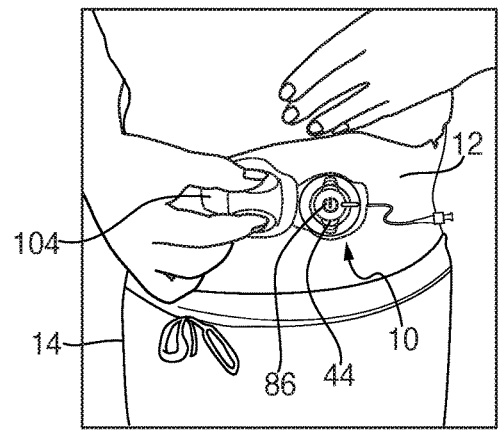

Referring now to FIGS. 3 and 6-9, an exemplary method of using the present infusion device 10 is illustrated. In FIG. 6, an adhesive backing 102 is removed from the adhesive layer 22 of the bottom surface 72. In FIG. 7, to secure the device 10 at the desired infusion site, the adhesive layer 22 side of the body is firmly pressed against the skin 12 of the patient 14 while holding an upper sterile cover or a blister package 104 of the infusion device 10. After successful attachment of the device 10, the sterile cover 104 is removed.

Figure 8:
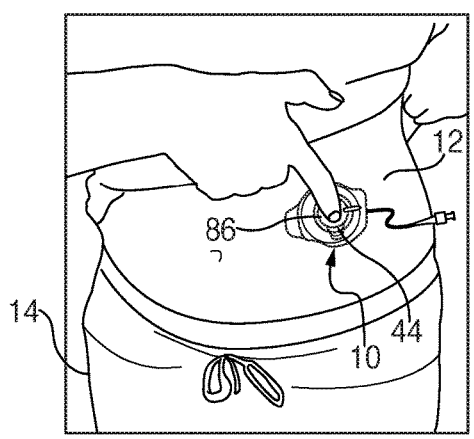
Figure 9:
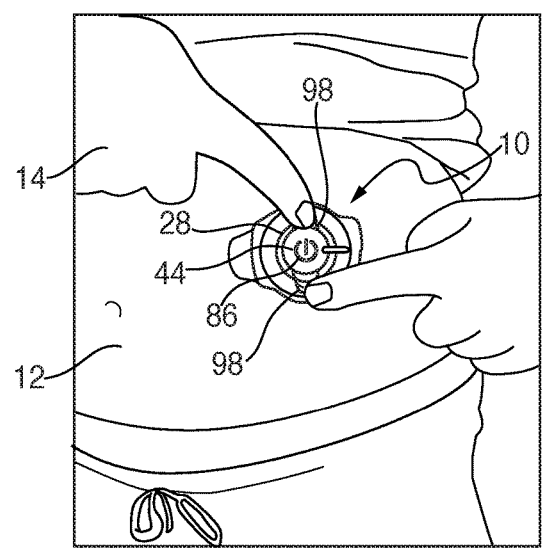

In FIG. 8 in conjunction with FIG. 5B, the press button 86 of the housing 44 is depressed downwardly such that the needle 42 penetrates the skin 12 for the delivery of the medicinal substances. In FIG. 9 in conjunction with FIG. 4B, after completion of the infusion therapy, the housing 44 is released by pushing the wing regions 98 of the receptacle member 28 downward resulting in the outward movement of the locking tab 94 and disengagement of the locking tab 94 and flange 90 whereby the housing 44 returns to its original configuration. The biasing member 50 forces the upward movement of the housing 44 until it recovers to its initial position, thereby automatically retracting the needle 42 from the skin 12.

While particular embodiments of the present infusion device have been shown and described, it will be appreciated by those skilled in the art that changes and modifications may be made thereto without departing from the present disclosure in its broader aspects and as set forth in the following claims.

What is claimed is:

1. A medical delivery device for delivering a medicinal substance into a user's body, comprising:
    an upper assembly including a housing having a cavity, and a needle disposed in said upper assembly;
    a lower assembly including
        a receptacle member having an opening configured for accommodating insertion of the housing of the upper assembly, and
        a base member having an upper body and a recess formed on a top surface of the upper body for receiving the receptacle member; and a base pad having an adhesive layer disposed on a lower surface of the pad, and being at least partially attached to a bottom side of the base member;
    a biasing member disposed in said receptacle member and engaging said housing for biasing said housing away from said base member; and
    a locking mechanism configured for releasably securing said housing in said lower position, said locking mechanism including at least one lower locking tab disposed on the receptacle member, and at least one corresponding upper locking tab disposed on the housing, such that when the tabs are in engagement, the housing is held in said lower position;
    wherein the lower assembly is attached to a skin of the user using the base pad, and as the upper assembly is urged by a pressing force by the user from an upper position to a lower position relative to the lower assembly and overcoming force exerted by the biasing member, in the lower position, the needle disposed in the upper assembly travels downwardly to penetrate the skin for facilitating administration of the medicinal substance.

2. The device of claim 1, wherein a first throughbore is disposed on a bottom side of said receptacle member, and a second throughbore is disposed on the bottom side of the base member, both the first and second throughbores being dimensioned for slidingly receiving the needle.

3. The device of claim 1, wherein the housing has a cylindrical column extending downwardly transverse to a top inner surface of the housing.

4. The device of claim 1, wherein the receptacle member has a tubular column extending upwardly transverse to a bottom side of the receptacle member.

5. The device of claim 1, wherein the housing has a first flange extending outwardly from an outer circumference of the housing, and a second flange extending inwardly from an outer circumference of the receptacle member.

6. The device of claim 1, wherein at least one wing region is disposed on the receptacle member and is connected to the at least one lower locking tab on the receptacle member such that actuation of the wing region releases the locking mechanism by moving said locking tabs out of engagement with each other, causing the biasing member to return the housing to the upper position.

7. The device of claim 1, wherein at least one of the receptacle member and the housing includes at least one guide rib extending in a direction of travel of said housing relative to said receptacle member for guiding the at least one of the receptacle member and the housing upon activation of the device.

8. The device of claim 1, wherein the adhesive layer includes and gradually releases at least one first active substance for preparing the skin for penetration prior to activation of the medical delivery device.

9. The device of claim 8, wherein the at least one first active substance includes an antiseptic agent.

10. The device of claim 1, wherein the adhesive layer includes and gradually releases at least one second active substance during the administration of the medical substance for enhancing general health of the skin at or near an infusion site.

11. The device of claim 10, wherein the at least one second active substance includes at least one of: an analgesic, a skin permeation enhancer, and a skin conditioning agent.

12. A medical delivery device for delivering a medicinal substance into a user's body, comprising:
an upper assembly including a housing having a cavity, and a needle disposed in said upper assembly;
a lower assembly including
a receptacle member having an opening configured for accommodating insertion of the housing of the upper assembly;
a base member having an upper body and a recess formed on a top surface of the upper body for receiving the receptacle member; and a base pad having an adhesive layer disposed on a lower surface of the pad, and being at least partially attached to a bottom side of the base member;
a biasing member disposed in the receptacle member and engaging the housing for biasing the housing away from the base member;
at least one lower locking tab on the receptacle constructed and arranged for releasably engaging an upper locking tab on the housing for securing the upper assembly in the lower position;
wherein the lower assembly is attached to a skin of the user using the base pad, and as the upper assembly is urged by the user from an upper position to a lower position relative to the lower assembly against force generated by the biasing member, the needle disposed in the upper assembly travels downwardly to penetrate the skin for facilitating administration of the medicinal substance, and the housing is releasably locked in position against action of the biasing member by engagement of said upper and lower locking tabs.

13. A medical delivery device for delivering a medicinal substance into a user's body, comprising:
an upper assembly including a housing having a cavity, and a needle disposed in said upper assembly;
a lower assembly including
a receptacle member having an opening configured for accommodating insertion of the housing of the upper assembly;
a base member having an upper body and a recess formed on a top surface of the upper body for receiving the receptacle member; and a base pad having an adhesive layer disposed on a lower surface of the pad, and being at least partially attached to a bottom side of the base member;
a biasing member disposed in the receptacle member and engaging the housing for biasing the housing away from the base member;
the upper assembly is urged by a pressing force by the user from an upper position to a lower position relative to the lower assembly and overcoming force exerted by the biasing member, in the lower position, the needle disposed in the upper assembly travels downwardly to penetrate the skin for facilitating administration of the medicinal substance;
at least one lower locking tab on the receptacle constructed and arranged for releasably engaging an upper locking tab on the housing for releasably securing said housing in said lower position; and
at least one wing region is disposed on the receptacle member and is connected to the at least one lower locking tab on the receptacle member such that actuation of the wing region releases the locking mechanism by moving said locking tabs out of engagement with each other, causing the biasing member to return the housing to the upper position.

14. A medical delivery device for delivering a medicinal substance into a user's body, comprising:
an upper assembly including a housing having a cavity, and a needle disposed in said upper assembly;
a lower assembly including
a receptacle member having an opening configured for accommodating insertion of the housing of the upper assembly, and
a base member having an upper body and a recess formed on a top surface of the upper body for receiving the receptacle member; and a base pad having an adhesive layer disposed on a lower surface of the pad, and being at least partially attached to a bottom side of the base member;
a biasing member disposed in said receptacle member and engaging said housing for biasing said housing away from said base member; and
a locking mechanism including at least one lower locking tab on said receptacle member configured for releasably engaging and securing said housing in said lower position; and
at least one wing region is disposed on the receptacle member and is connected to said at least one lower locking tab on the receptacle member such that actuation of the wing region releases the locking mechanism by moving said at least one locking tab out of engagement with said housing, causing the biasing member to return the housing to the upper position;
wherein the lower assembly is attached to a skin of the user using the base pad, and as the upper assembly is urged by a pressing force by the user from an upper position to a lower position relative to the lower assembly and overcoming force exerted by the biasing member, in the lower position, the needle disposed in the upper assembly travels downwardly to penetrate the skin for facilitating administration of the medicinal substance.

15. The device of claim 14, wherein a first throughbore is disposed on a bottom side of said receptacle member, and a second throughbore is disposed on the bottom side of the base member, both the first and second throughbores being dimensioned for slidingly receiving the needle.

16. The device of claim 14, wherein the housing has a cylindrical column extending downwardly transverse to a top inner surface of the housing.

17. The device of claim 14, wherein the receptacle member has a tubular column extending upwardly transverse to a bottom side of the receptacle member.

18. The device of claim 14, wherein the housing has a first flange extending outwardly from an outer circumference of the housing, and a second flange extending inwardly from an outer circumference of the receptacle member.

19. The device of claim 14, wherein at least one of the receptacle member and the housing includes at least one guide rib extending in a direction of travel of said housing relative to said receptacle member for guiding the at least one of the receptacle member and the housing upon activation of the device.

20. The device of claim 14, wherein the adhesive layer includes and gradually releases at least one second active substance during the administration of the medical substance for enhancing general health of the skin at or near an infusion site, wherein the at least one second active substance includes at least one of: an analgesic, a skin permeation enhancer, and a skin conditioning agent.

\* \* \* \* \*